United States Patent
Conn et al.

(10) Patent No.: US 7,838,291 B2
(45) Date of Patent: Nov. 23, 2010

(54) ENTRAPPED STEM CELLS AND USES THEREOF

(75) Inventors: Bryan Conn, New York, NY (US);
Barry Smith, New York, NY (US);
Albert L. Rubin, Engelwood, NJ (US);
Kurt Stenzel, New York, NY (US)

(73) Assignee: The Rogosin Institute, New York, NY (US)

( * ) Notice: Subject to any disclaimer, the term of this patent is extended or adjusted under 35 U.S.C. 154(b) by 301 days.

(21) Appl. No.: 11/891,526

(22) Filed: Aug. 10, 2007

(65) Prior Publication Data
US 2008/0020463 A1 Jan. 24, 2008

Related U.S. Application Data

(63) Continuation of application No. 10/655,275, filed on Sep. 4, 2003, now abandoned.

(51) Int. Cl.
*C12N 5/00* (2006.01)
*C12N 5/02* (2006.01)

(52) U.S. Cl. .................. 435/374; 435/375; 435/377; 435/382; 435/395

(58) Field of Classification Search .................. None
See application file for complete search history.

(56) References Cited

U.S. PATENT DOCUMENTS

2003/0119107 A1 * 6/2003 Dang et al. ............... 435/69.1
2007/0186293 A1 * 8/2007 Teratani et al. ............... 800/14

OTHER PUBLICATIONS

Dang et al. (2004) Controlled, scalable embryonic stem cell differentiation culture. Stem Cells 22: 275-282.*
Weber et al. (2002) Formation of cartilage matrix proteins by BMP-transfected murine mesenchymal stem cells encapsulated in a novel class of alginates. Biomaterials 23: 2003-2013.*

* cited by examiner

*Primary Examiner*—Anne-Marie Falk
(74) *Attorney, Agent, or Firm*—Fulbright & Jaworski, LLP

(57) ABSTRACT

The invention relates to the stem cells, embryonic stem cells in particular. It has been found that, when these stem cells are entrapped such that their proliferation is inhibited, they produce material which inhibits the proliferation of other, non-entrapped cells, including stem cells and neoplastic and/or hyperproliferative, but otherwise normal cells. It has also been found that entrapped cancer cells will produce material which inhibits the proliferation of stem cells. Further, it has been found that the entrapment of the stem cells inhibits their differentiation and thus the entrapment process can serve as a long-term storage device for maintaining the undifferentiated state of at least a portion of the entrapped cells.

8 Claims, No Drawings

ENTRAPPED STEM CELLS AND USES THEREOF

RELATED APPLICATION(S)

This application is a continuation of application Ser. No. 10/655,275, filed Sep. 4, 2003, now abandoned, incorporated by reference in its entirety.

FIELD OF THE INVENTION

This invention relates to entrapped cells, such as stem cells. The entrapped cells, when cultured in the entrapment material, produce a product which, when it is in contact with other non-entrapped, freely growing cells in vitro or in vivo, inhibits their proliferation. Further, the entrapment of the stem cells acts to inhibit the proliferation of at least some of the entrapped stem cells, and may inhibit the differentiation of at least a portion of the entrapped stem cells.

BACKGROUND AND PRIOR ART

Entrapment of biological materials, such as cells, is a technique that has been used for various ends. Exemplary of the patent literature in this area are U.S. Pat. No. 6,303,151 (Asina, et al.); U.S. Pat. No. 6,224,912 (Asina, et al.); U.S. Pat. No. 5,888,497 (Jain, et al.); U.S. Pat. No. 5,643,569 (Jain, et al.), and RE 38,027 (Jain, et al.), all of which are incorporated by reference in their entirety. This family of related patents shows that cancer cells and islets can be entrapped in a biocompatible matrix, such as agarose, agarose/collagen mixtures, and agarose/gelatin mixtures, and then be coated with agarose. The resulting, entrapped cells produce materials which, inter alia, diffuse out of the permeable biocompatible matrices in which they are retained, and have useful biological properties. In the case of islets, insulin is produced. In the case of cancer cells, material diffuses from the matrix, and this material has an effect on the growth and proliferation of cancer cells. As review of the '912 and '151 patents, cited supra, will show, this effect crosses species, i.e., entrapped or encapsulated cancer cells from a given species produce material that inhibits the growth and/or proliferation of cancer cells from other species, as well as the species from which the cancer cells originated.

Additional examples of entrapment techniques include, e.g., U.S. Patent No. 5,227,298 (Weber, et al.); U.S. Pat. No. 5,053,332 (Cook, et al.); U.S. Pat. No. 4,997,443 (Walthall, et al.); U.S. Pat. No. 4,971,833 (Larsson, et al.); U.S. Pat. No. 4,902,295 (Walthall, et al.); U.S. Pat. No. 4,798,786 (Tice, et al.); U.S. Pat. No. 4,673,566 (Goosen, et al.); U.S. Pat. No. 4,647,536 (Mosbach, et al.); U.S. Pat. No. 4,409,331 (Lim); U.S. Pat. No. 4,392,909 (Lim); U.S. Pat. No. 4,352,883 (Lim); and, U.S. Pat. No. 4,663,286 (Tsang, et al.). All of these references are incorporated by reference.

Entrapment does not always result in a positive impact on the entrapped cells. For example, see Lloyd-George, et al., *Biomat. Art. Cells & Immob. Biotech.*, 21(3):323-333 (1993); Schinstine, et al., *Cell Transplant*, 41(I):93-102 (1995); Chicheportiche, et al., *Diabetologica*, 31:54-57 (1988); Jaeger, et al., *Progress In Brain Research*, 82:41-46 (1990); Zekorn, et al., *Diabetologica*, 29:99-106 (1992); Zhou, et al., *Am. J. Physiol.*, 274:C1356-1362 (1998); Darquy, et al., *Diabetologica*, 28:776-780 (1985); Tse, et al., *Biotech. & Bioeng.*, 51:271-280 (1996): Jaeger, et al., *J. Neurol.*, 21-469-480 (1992); Hortelano, et al., *Blood*, 87(12):5095-5103 (1996): Gardiner, et al., *Transp. Proc.*, 29:2019-2020 (1997). All of these references are incorporated by reference.

None of the references discussed supra deals with the class of cells known as stem cells, including embryonic stem cells.

One definition of stem cells, advanced by Reya, et al., *Nature*, 414:105-111 (2001), incorporated by reference, refers to stems cells as cells which have the ability to perpetuate themselves through self renewal and to generate mature cells of particular tissues via differentiation. One can obtain different types of stem cells, including neural, hematolymphoid, myeloid, and other types of stem cells from various organs. These all have potential to develop into specific organs or tissues. Certain stem cells, such as embryonic stem cells, are pluripotent, in that their differentiation path has not been determined at all, and they can develop into various organs and tissues.

The discussions of the various therapeutic uses to which stem cells may be put are well known, and need not be discussed here. It is worth mentioning, as it bears on the invention described herein, that stem cells are very uncommon, their purification and separation from other cell types is laborious and difficult, and stem cells will differentiate into mature cell unless treated in some way to prevent this.

It has now been found that entrapment procedures, in line with those disclosed by Jain et al. and Iwata et al., *Journ. Biomedical Material and Res.*, 26:967 (1992) affect stem cells in a very desirable way. To elaborate, entrapped stem cells produce materials which inhibit proliferation of various cell types, including stem cells and cancer cells. The effect of this material crosses species lines. Further, it has been found that stem cells, when entrapped as is described herein, retain their differentiating abilities, including their pluripotentiality, for an indefinite period of time.

These features, as well as others, will be seen in the disclosure which now follows.

DETAILED DESCRIPTION OF THE PREFERRED EMBODIMENTS

Example 1

Two different murine embryonic stem (ES) cell lines (i.e., ES-D3 and SCC-PSA1, which are both publicly available) were obtained from the American Type Culture Collection ("ATCC").

Both lines were grown under standard culture conditions, which included growth as a monolayer, atop "STO" embryonic fibroblast feeder cells. These were also obtained from the ATCC. The stem cells were cultured in DMEM medium that had been supplemented with 100% ES-Qualified fetal bovine serum, leukemia inhibitory factor (LIF), and β-mercaptoethanol (collectively, "Medium A"). The cells, which were cryopreserved when received, were thawed, and established as cultures after at least 3 passages before being cultured as described, supra.

After three days, the ES cells were 70-80% confluent, and were trypsinized and then entrapped in agarose beads, coated with agarose, in accordance with U.S. Pat. Nos. 6,303,151; 6,224,912; and, 5,888,497, all of which are incorporated by reference. In brief, however, Sigma XII agarose was used, at an initial concentration of about 1.0%. A 100 μl aliquot of this agarose solution was added to 34 μl of cell suspension. The resulting beads contained $2.0 \times 10^5 \pm 1.5 \times 10^4$ murine embryonic stem cells. The beads were given a second coat of agarose, at a concentration of about 5.0%. The beads were cultured in medium as described supra, except no LIF or viable STO feeder cells were present ("Medium B").

The viability of cells in the beads over time was assessed, via standard histochemical and microscopic examination, as well as standard MTT assays, using cells removed from beads or maintained in the beads, at various points in time.

It was observed that entrapped stem cells increase their metabolic activity when first coated. This is followed by a decrease in activity, as cells die via apoptosis, reaching their lowest point of metabolic activity around day 21. After this low point, however, surviving cells slowly proliferate, and total metabolic activity was seen to gradually increase up to day 35 post entrapment and beyond. This parallels observations on entrapped cancer cells.

Morphologically, there was a significant difference between the colonies formed within the inner layer of agarose of the bead by the cancer cells and those formed by the stem cells. Although both types of colonies are ovoid in shape, those formed by the cancer cells are characterized by an outer zone of viable cells (generally two to three cells in thickness) with a central zone of eosiniphilic cellular debris. The colonies formed by the stem cells, on the other hand, are fully occupied by viable cells and there is no central zone of cellular debris.

Example 2

In these experiments, the inhibitory effect of stem cells on the proliferation of other stem cells was tested.

Ten-week-old agarose/agarose beads containing stem cells (SCC-PSA1 cells) were tested for viability using the MTT assay, discussed supra, and were cultured in Medium B discussed in example 1, for 6 days. After 6 days, the medium had been conditioned by the entrapped stem cells. It is therefore called the Stem-cell Conditioned Medium (SCM).

After these 6 days, the SCM was transferred to 6 well plates that contained fresh SCC-PSA1 cells. These plates each contained $9\times10^5$ STO feeder cells, which were covered with $1.5\times10^4$ SCC-PSA1 cells. The STO cells had been treated with mitomycin C to prevent proliferation. There were three controls, i.e., wells which contained Medium B (an unconditioned medium), and three wells that contained the SCM.

After 3 days, the contents of all wells were trypsinized, and total cells were counted, using standard methods. The raw count was adjusted to account for the $9\times10^5$ feeder cells. The results follow:

| Test Article | Average Total Cells/Well | Standard Deviation | Cells After subtracting STO | Percent Inhibition (of SCC cells) |
|---|---|---|---|---|
| Control Medium | $1.43\times10^6$ | $\pm9.9\times10^4$ | $5.27\times10^5$ | |
| SCM (w/SCC) | $1.19\times10^6$ | $\pm3.6\times10^4$ | $2.90\times10^5$ | 44.9% |

A similar experiment was carried out, with the following results:

| | | | | |
|---|---|---|---|---|
| Control Medium | $3.09\times10^6$ | $\pm1.7\times10^5$ | $1.41\times10^6$ | |
| SCM (w/SCC) | $2.36\times10^6$ | $\pm9.5\times10^4$ | $6.88\times10^5$ | 51.4% |

Further, the effect was not cell-line specific, as is demonstrated by the following results, where ES-D3 cells were added to the medium:

| Test Article | Average Total Cells/Well | Standard Deviation | Cells After subtracting STO | Percent Inhibition (of ES-D3 cells) |
|---|---|---|---|---|
| Control Medium | $1.27\times10^6$ | $\pm1.1\times10^5$ | $3.67\times10^5$ | |
| SCM (w/SCC) | $1.14\times10^6$ | $\pm7.6\times10^4$ | $2.37\times10^5$ | 35.5% |

Example 3

Example 2 showed that the proliferation inhibitory effect of the stem cells was not cell line specific. In the experiments described herein, the entrapped stem cells were tested for their ability to inhibit the proliferation of cancer cells.

In these experiments, RENCA tumor cells were used. A total of 15,000 tumor cells were seeded per well. SCM (conditioned either with SCC-PSAI or ES-D3), as described supra, was used, as was the control medium (Medium B), also as described.

With respect to the SCM, the conditioning took place over 5 days. The assay was run over a period of 32 weeks. The inhibition of the RENCA cells was determined by fixing the cells with 100% methanol, followed by staining with neutral red, lysis with SDS, and scanning with a spectrophotometer to measure the amount of neutral red in the cell lysate, which is proportional to the number of cells per well.

The results are summarized in the following two tables, which represent work with ES-D3, and SCC-PSA1 stem cells, respectively. The results for weeks 1-3 correlate with the results discussed in example 1, i.e., death of the entrapped stem cells, reaching a low point on day 21, followed by regeneration.

| | Week | | | | | | |
|---|---|---|---|---|---|---|---|
| | 1 | 3 | 12 | 16 | 20 | 24 | 28 | 32 |
| % Inhibition of RENCA Cells by SCM (W/ES-D3) | −2.1% | −8.8% | 39.0% | 24.4% | 25.0% | 20.9% | 34.9% | 31.5% |

| | Week | | | | | | | |
|---|---|---|---|---|---|---|---|---|
| | 1 | 3 | 9 | 12 | 16 | 20 | 24 | 28 | 32 |
| % Inhibition of RENCA Cells by SCM (w/SCC-PSA1) | −10.0% | 8.9% | 21.0% | 40.4% | 32.8% | 22.5% | 36.6% | 38.0% | 35.1% |

Example 4

In the preceding experiments, the ability of entrapped stem cells to inhibit proliferation of stem cells and cancer cells was tested, and proven. These next experiments were designed to determine if entrapped cancer cells could inhibit the proliferation of stem cells.

Stem cells were plated and cultured in the same way as was described, supra. RENCA cell containing beads, prepared as described in U.S. Pat. Nos. 6,303,151; 6,224,912; and, 5,888, 497 were cultured in Medium B to condition it, for 5 days. This RENCA Conditioned Medium (RCM) was then added to plated stem cells, and the stem cells were counted after 3 days. The results, which follow, present data for ES-D3 cells first, and then SCC-PSA1 cells:

| Test Article | Average Total Cells/Well | Standard Deviation | Cells After subtracting STO | Percent Inhibition (of ES-D3) |
|---|---|---|---|---|
| Control Medium | $1.69 \times 10^6$ | $\pm 1.15 \times 10^4$ | $7.93 \times 10^5$ | |
| RCM | $1.42 \times 10^6$ | $\pm 8.7410^4$ | $5.23 \times 10^5$ | 34.0% |

| Test Article | Average Total Cells/Well | Standard Deviation | Cells After subtracting STO | Percent Inhibition (of SCC-PSA1) |
|---|---|---|---|---|
| Control Medium | $1.25 \times 10^6$ | $\pm 8.08 \times 10^4$ | $3.47 \times 10^5$ | |
| RCM | $1.05 \times 10^6$ | $\pm 4.04 \times 10^4$ | $1.47 \times 10^5$ | 57.7% |

These results indicate that the entrapped cancer cells did inhibit the proliferation of stem cells.

Example 5

One issue with stem cell research is the fact that, by their nature, stem cells differentiate. As it is difficult to secure stem cells and keep them from differentiating in the first place, it would be desirable to have a methodology available by which stem cells could be kept in their undifferentiated state, for as long a period as possible.

To this end, stem cells were entrapped as described in example 1, supra. The resulting structures were stored in Medium B described supra, and were tested over a period of more than two years.

Over this two-year period, stem cells were released from the entrapment structures and cultured under standard conditions (including STO co-cultures and LIF media additive). In all cases, the released cells established a traditional stem cell monolayer that proliferated in a non-differentiated manner, but maintained the capability to spontaneously differentiate. This demonstrates that the entrapment of stem cells can maintain their non-differentiated phenotypes for greater than two years in the absence of the traditionally required inhibitors of differentiation (e.g., STO and LIF).

Notwithstanding this fact, if the cells do not receive the required materials after a short period of time, they do begin differentiation.

The foregoing examples describe the invention, which includes, inter alia, compositions of matter which can be used to produce material which suppresses proliferation of cells, Such as, but not being limited to, cancer cells and stem cells. These compositions comprise stem cells, such as embryonic stem cells, entrapped in a selectively permeable material to form a structure which restricts the proliferation of the entrapped cells. As a result of their being restricted, the cells produce unexpectedly high amounts of material which suppresses proliferation of other cells. The restricted cells produce more of the material than comparable, non-restricted cells.

The material used to make the structures of the invention may include any biocompatible matter which restricts the growth of stem cells, thereby inducing them to produce greater amounts of cell proliferation growth-suppressing material. The structure has a suitable pore size such that the above material can diffuse to the external environment, and such that it can prevent products or cells from the immune system of the host from entering the structure and causing the rejection of the cells or otherwise impair their ability to survive and continue to produce the desired material. The materials used to form the structure will also be capable of maintaining viable (proliferation-restricted, but surviving) cells both in vitro and in vivo, preferably for periods of up to several years, by providing for the entrance of proper nutrients, and elimination of cellular waste products, and a compatible physico-chemical intrastructural environment. The resulting structures provide an environment suitable for the extended study of stem cells and their various differentiation, transcription and nuclear factors. Results therefrom can be used to direct the desired differentiation of other stem cells. The materials used to prepare the structure is preferably well tolerated when implanted in vivo, most preferably for the entire duration of implantation in the host.

A non-limiting list of materials and combinations of materials that might be utilized includes alginate-poly-(L-lysine); alginate-poly-(L-lysine)-alginate; alginate-poly-(L-lysine)-polyethyleneimine; chitosan-alginate; polyhydroxylethyl-methacrylate-methyl methacrylate; carbonylmethylcellulose; K-carragenan; chitosan; agarose-polyethersulphone-hexadi-methirine-bromide (Polybrene); ethyl-cellulose; silica gels; and combinations thereof.

The structures which comprise the compositions of matter may take many shapes, such as a bead, a sphere, a cylinder, a capsule, a sheet or any other shape which is suitable for implantation in a subject, and/or culture in an in vitro milieu. The size of the structure can vary, depending upon its eventual use, as will be clear to the skilled artisan.

The structures of the invention are selectively permeable, such that nutrients may enter the structure, and so that the proliferation-inhibiting material as well as cellular waste may leave the structure. For in vivo use, it is preferred that the structures prevent the entry of products or cells of the immune system of a host which would cause the rejection of the cells, or otherwise impair the ability of the cells to produce the proliferation-suppressive material.

"Entrapped" as used herein means that the cells are contained within a structure which prevents their escape to the environment surrounding the structure, be that an in vitro or in vivo environment. Notwithstanding the inability to escape therefrom, the cells are within a structure which both permits entry of molecules such as water, nutrients, and so forth, and permits the passage from the structure of waste materials and molecular products produced by the cells. The structure in which the cells are contained thus supports the continued viability/survival of the cells for long periods of time. It may also, depending on the nature of the structure/material, cause the cells contained within it to alter their behavior, including, but not limited to, such behavior as proliferation, state of differentiation and/or phenotypic expression. By inhibiting differentiation, one de facto has a storage device useful for maintaining stem cells as stem cells. Exemplary, but nonexclusive, means of entrapping the cells include encapsulating them, encasing them, enclosing them, or otherwise surrounding them on all sides with some permeable material. Via the entrapment, the proliferation of the entrapped stem cells is inhibited. Further, there are situations where at least a portion of the population that is entrapped does not undergo any differentiation as well.

Another aspect of the invention includes compositions which are useful in suppressing cell proliferation. The compositions are prepared by culturing restricted cells as described supra in an appropriate culture medium, followed by recovery of the resultant conditioned medium. Concentrates can then be formed from the conditioned medium.

The invention is not limited to any particular type of stem cell species; any stem cell type may be used in accordance with the invention. Exemplary types of cells which can be used are human or murine stem cells, as well as stem cells from other species, especially mammalian species. Embryonic stem cells are especially preferred, but stem cells obtained from various organs and/or organ systems may be used as well.

As will be clear from this disclosure, a further aspect of the invention is therapeutic methods for treating individuals suffering from cell proliferation disorders such as polycystic kidney disease, hypertrophic tissue reaction (including scar formation), autoimmune disease, lympho-proliferative disorders, polycythemia vera, as well as both benign and malignant cell neoplasia. When used in a therapeutic context, as will be elaborated upon infra, the type of cell restricted in the structure need not be the same type of cell that is causing the disorder from which the individual is suffering, although it can be. One such method involves inserting at least one of the structures of the invention into the subject, in an amount sufficient to cause suppression of cell proliferation in the subject. Preferably, the subject is a human being, although it is applicable to other animals, such as domestic animals, farm animals, or any type of animal.

The composition of the present invention can be used as primary therapy in the treatment of various cell proliferative disorders, and as an adjunct treatment in combination with other therapies. For example, in neoplastic disorders, such as cancer, patients may be treated with compositions and methods described herein, in conjunction with radiation therapy, chemotherapy, or treatment with other biologically active materials such as cytokines, anti-sense molecules, steroid hormones, gene therapy, and the like. Additionally, the compositions and methods of the invention can be used in conjunction with surgical procedures to treat disorders such as cancer, e.g., by implanting the structures after resection of a tumor to prevent regrowth and metastases. Cancers which are present in an inoperable state may be rendered operable by treatment with the anti-proliferative compositions of the invention. The excess proliferation of cells that are not needed or desirable for proper organ system function, but are not neoplastic, such as that of polycythemia vera or polycystic kidney disease, may also be treated by this means. Hyperproliferative disorders, such as polycythermia vera and polycystic kidney disease, involve cells that exhibit excess proliferation but generate otherwise normal (i.e., non-neoplastic or transformed) cells. Such disorders, resulting in numerous cells that are not needed or desirable for proper organ function, may also be treated by these means. Additionally, conditions which are characterized by hyperproliferative, normal cells, such as hypertrophic scars, can also be treated in this way. In conditions such as this one, normal cells, i.e., fibroblasts have proliferated beyond what is necessary for healing, but unlike neoplasias, they are not characterized by further, ongoing, unregulated proliferation. Other conditions characterized by this phenomenon well known to the skilled artisan, and need not be set forth here.

The compositions of the invention can also be used prophylactically in individuals at risk for developing cell proliferation disorders, subjects who show the presence of individual risk factors, a family history of the disorder generally, family history of a specific type (e.g., breast cancer), and exposure to occupational or other problematic materials. For prophylaxis against cancer, e.g., a prophylactically effective amount of the structures of the invention are administered to the individual upon identification of one or more risk factors.

As indicated by the examples, supra, the antiproliferative effect is not limited by the type of cell used, nor by the species from which the stem cell originated. Hence, one can administer structures which contain stem cells of a first type to a subject of a different species. For example, murine stem cells may be restricted in the structure of the invention, and then be administered to a human. Of course, the structures may contain stem cells from the same species as is being treated. Still further, the stem cell may be taken from the individual to be treated, entrapped and restricted, and then administered to the same individual.

Processes for making the structures of the invention are also a part of the invention.

Other facets of the invention will be clear to the skilled artisan, and need not be set out here.

The terms and expression which have been employed are used as terms of description and not of limitation, and there is no intention in the use of such terms and expression of excluding any equivalents of the features shown and described or portions thereof, it being recognized that various modifications are possible within the scope of the invention.

We claim:

1. A process of inhibiting differentiation of at least portion of a population of mammalian stem cells, comprising entrapping said population of mammalian stem cells in agarose which is coated with agarose and storing said entrapped population of mammalian stem cells in a culture medium to inhibit differentiation of at least a portion of said population.

2. The process of claim 1, wherein said mammalian stem cells human stem cells.

3. The process of claim 1, wherein said mammalian cells are murine stem cells.

4. The process of claim 1, wherein said stem cells are embryonic stem cells.

5. The process of claim 1, wherein said stem cells are entrapped in a mixture of agarose and collagen or a mixture of agarose and gelatin.

6. The method of claim 1, wherein said entrapped population of stem cells are stored in an LIF free, STO feeder cell free medium.

7. The method of claim 6, wherein said entrapped population of stem cells are stored for over two years, prior to release from said agarose coated with agarose.

8. The method of claim 1, wherein said population of stem cells is entrapped by a bead consisting of agarose which is coated with agarose.

* * * * *